United States Patent
Okahara et al.

(10) Patent No.: US 11,319,369 B2
(45) Date of Patent: May 3, 2022

(54) MOTOR CONTROL FUNCTION IMPROVING AGENT

(71) Applicant: Kao Corporation, Tokyo (JP)

(72) Inventors: Fumiaki Okahara, Utsunomiya (JP); Yoshitaka Koga, Utsunomiya (JP); Takuya Mori, Utsunomiya (JP)

(73) Assignee: Kao Corporation, Tokyo (JP)

( * ) Notice: Subject to any disclaimer, the term of this patent is extended or adjusted under 35 U.S.C. 154(b) by 201 days.

(21) Appl. No.: 16/471,730

(22) PCT Filed: Dec. 26, 2017

(86) PCT No.: PCT/JP2017/046526
§ 371 (c)(1),
(2) Date: Jun. 20, 2019

(87) PCT Pub. No.: WO2018/124011
PCT Pub. Date: Jul. 5, 2018

(65) Prior Publication Data
US 2019/0330334 A1    Oct. 31, 2019

(30) Foreign Application Priority Data
Dec. 26, 2016   (JP) .............................. JP2016-251777

(51) Int. Cl.
| | |
|---|---|
| *A61P 21/00* | (2006.01) |
| *A61P 25/28* | (2006.01) |
| *A61K 9/00* | (2006.01) |
| *C07K 16/26* | (2006.01) |
| *A61K 31/15* | (2006.01) |

(Continued)

(52) U.S. Cl.
CPC .............. *C07K 16/26* (2013.01); *A61K 31/15* (2013.01); *A61K 31/404* (2013.01); *A61K 36/07* (2013.01); *A61K 36/899* (2013.01); *A61P 21/00* (2018.01); *A61K 2039/505* (2013.01)

(58) Field of Classification Search
None
See application file for complete search history.

(56) References Cited

U.S. PATENT DOCUMENTS

| | | |
|---|---|---|
| 2005/0159415 A1 | 7/2005 | Tsubamoto et al. |
| 2008/0306030 A1 | 12/2008 | Lee et al. |

(Continued)

FOREIGN PATENT DOCUMENTS

| | | |
|---|---|---|
| CN | 101626770 A | 1/2010 |
| EP | 1 506 777 A1 | 2/2005 |

(Continued)

OTHER PUBLICATIONS

Wozniak et al., Juice concentrated of edible mushrooms. Karstenia 18(suppl.) 1978, 102-105 (Year: 1978).*

(Continued)

*Primary Examiner* — Aurora M Fontainhas
(74) *Attorney, Agent, or Firm* — Sterne, Kessler, Goldstein & Fox P.L.L.C.

(57) ABSTRACT

Provided are a motor control function improving agent for improving a motor control function decreased by aging or tiredness and a method for evaluating or selecting the motor control function improving agent. The motor control function improving agent comprises a GIP function inhibitor as an active ingredient.

2 Claims, 3 Drawing Sheets

Specification includes a Sequence Listing.

(51) Int. Cl.
*A61K 31/404* (2006.01)
*A61K 36/07* (2006.01)
*A61K 36/899* (2006.01)
*A61K 39/00* (2006.01)

(56) References Cited

U.S. PATENT DOCUMENTS

2017/0369569 A1  12/2017  Fukuoka et al.
2019/0330332 A1  10/2019  Okahara et al.

FOREIGN PATENT DOCUMENTS

| JP | 2006-342084 A | 12/2006 |
| JP | 2009-263344 A | 11/2009 |
| JP | 2013-138638 A | 7/2013 |
| JP | 2014-084280 A | 5/2014 |
| WO | WO 03/097031 A1 | 11/2003 |
| WO | WO 2016/104439 A1 | 6/2016 |
| WO | WO 2018/124009 A1 | 7/2018 |

OTHER PUBLICATIONS

International Search Report (ISR) for PCT/JP2017/046526; I.A. fd Dec. 26, 2017, dated Apr. 10, 2018 from the Japan Patent Office, Tokyo, Japan.
International Preliminary Report on Patentability (IPRP), Chapter I of the Patent Cooperation Treaty, including the Written Opinion for PCT/JP2017/046526; I.A. fd Dec. 26, 2017, dated Jul. 2, 2019, by the International Bureau of WIPO, Geneva, Switzerland.
Uchiyama, Yasushi et al., "Zenteimeiro-sei Sikkan ni tomonau Memai/Heiko shogai Kanja No. Undo Ryoho (Exercise therapy of dizziness and dysequilibrium patients due to vestibular labyrinthine disease)", Equilibrium Research. 50(2): 199-205, 1991.
Miyawaki, K et al., "Inhibition of gastric inhibitory polypeptide signaling prevents obesity," Nat Med. Jul. 2002;8(7):738-42. Epub Jun. 17, 2002.
Thangthaeng, N et al, "Daily supplementation with mushroom (*Agaricus bisporus*) improves balance and working memory in aged rats," Nutr Res. Dec. 2015;35(12):1079-84. doi: 10.1016/j.nutres. 2015.09.012. Epub Oct. 5, 2015.
Kalyani, RR et al., "Diabetes and altered glucose metabolism with aging," Endocrinol Metab Clin North Am. Jun. 2013;42(2):333-47. doi: 10.1016/j.ecl.2013.02.010. Epub Mar. 22, 2013.
Weiss, EP et al., Calorie Restriction and Matched Weight Loss From Exercise: Independent and Additive Effects on Glucoregulation and the Incretin System in Overweight Women and Men, Diabetes Care. Jul. 2015;38(7):1253-62. doi: 10.2337/dc14-2913. Epub Apr. 15, 2015.
Han, S et al., "Dietary fiber prevents obesity-related liver lipotoxicity by modulating sterol-regulatory element binding protein pathway in C57BL/6J mice fed a high-fat/cholesterol diet," Sci Rep. Oct. 29, 2015,5:15256. doi: 10.1038/srep15256.
Kelly, KR et al., "The glucose-dependent insulinotropic polypeptide and glucose-stimulated insulin response to exercise training and diet in obesity," Am J Physiol Endocrinol Metab. Jun. 2009;296(6):E1269-74. doi: 10.1152/ajpendo.00112.2009. Epub Apr. 7, 2009.
Extended European search report including the supplementary European search report and the European search opinion, for EP Appl. No. 17888377.3, dated Oct. 20, 2020.
Zhang, C.Y. et al., "Effects of gastric inhibitory polypeptide (GIP) immunoneutralization on mouse motor coordination and memory." Peptides. Mar. 2020;125:170227. doi: 10.1016/j.peptides.2019. 170227. Epub Dec. 2, 2019. PMID: 31805296.
McClean PL, et al.,"GIP receptor antagonism reverses obesity, insulin resistance, and associated metabolic disturbances induced in mice by prolonged consumption of high-fat diet." Am J Physiol Endocrinol Metab. Dec. 2007;293(6):E1746-55. doi: 10.1152/ajpendo. 00460.2007. Epub Sep. 11, 2007. PMID: 17848629.
Hansotia T, et al., "Extrapancreatic incretin receptors modulate glucose homeostasis, body weight, and energy expenditure." J Clin Invest. Jan. 2007;117(1):143-52. doi: 10.1172/JCI25483. Epub Dec. 21, 2006. PMID: 17187081; PMCID: PMC1705821.
Wei Bao-Yao et al., ["*Agaricus bisporus* (Lange) Sing polysaccharide anti-bacterial reactive and to curb corruption in the food research."] Food Science and Technology No. 3, pp. 93-95, Dec. 31, 2007, doi: 10.13684/j.cnki.spkj.2007.04.029.
Li Li et al., ["Study on the hypoglycemic effect of wheat bran dietary fiber on mice,"] Cereal and food industry, vol. 17 , No. 3, pp. 30-32, Dec. 31, 2010.
Sugi, Haruo, et al., "Zintai Kinou Seirigaku (Physiology of Human Body Functions), 5th revision," Nanzando, 2010, pp. 218-225.
Kato, Motohiro, Jibito Rinsho 32:1097-1102, 1986.
Matsunaga, Takashi "Memai ni taisuru Yakubutsu Ryoho no Sentaku to Koka (Selection and effect of drug therapy on dizziness)," Jibi Rinsho, 65 (Special issue 1): 653-671, 1972.

* cited by examiner

SEQUENCE LISTING

<160> NUMBER OF SEQ ID NOS: 6

<210> SEQ ID NO 1
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 1

| cag | gtc | caa | ctg | cag | cag | cct | ggg | gct | gaa | ctg | gtg | aag | cct | ggg | gcc | 48 |
| Gln | Val | Gln | Leu | Gln | Gln | Pro | Gly | Ala | Glu | Leu | Val | Lys | Pro | Gly | Ala | |
| 1   |     |     |     | 5   |     |     |     |     | 10  |     |     |     |     | 15  |     | |

| tca | gtg | aag | ctg | tcc | tgc | aag | gct | tct | ggc | tac | acc | ttc | acc | agc | ttc | 96 |
| Ser | Val | Lys | Leu | Ser | Cys | Lys | Ala | Ser | Gly | Tyr | Thr | Phe | Thr | Ser | Phe | |
|     |     |     | 20  |     |     |     |     | 25  |     |     |     |     | 30  |     |     | |

| tgg | atg | cac | tgg | gtg | att | cag | agg | cct | gga | caa | ggc | ctt | gag | tgg | att | 144 |
| Trp | Met | His | Trp | Val | Ile | Gln | Arg | Pro | Gly | Gln | Gly | Leu | Glu | Trp | Ile | |
|     |     | 35  |     |     |     |     | 40  |     |     |     |     | 45  |     |     |     | |

| gga | gag | atg | aat | cct | agc | gac | ggt | cgt | act | cac | ttc | aat | gaa | aag | ttc | 192 |
| Gly | Glu | Met | Asn | Pro | Ser | Asp | Gly | Arg | Thr | His | Phe | Asn | Glu | Lys | Phe | |
|     | 50  |     |     |     |     | 55  |     |     |     |     | 60  |     |     |     |     | |

| aag | acc | aag | gcc | aca | ctg | act | ata | gac | aca | tcc | tcc | aac | aca | gcc | tac | 240 |
| Lys | Thr | Lys | Ala | Thr | Leu | Thr | Ile | Asp | Thr | Ser | Ser | Asn | Thr | Ala | Tyr | |
| 65  |     |     |     |     | 70  |     |     |     |     | 75  |     |     |     |     | 80  | |

| atg | gaa | ctc | aac | agc | ctg | aca | tct | gag | gac | tct | gcg | gtc | tat | tac | tgt | 288 |
| Met | Glu | Leu | Asn | Ser | Leu | Thr | Ser | Glu | Asp | Ser | Ala | Val | Tyr | Tyr | Cys | |
|     |     |     |     | 85  |     |     |     |     | 90  |     |     |     |     | 95  |     | |

| gca | aga | agg | atg | gag | gac | tgg | ggc | caa | ggg | act | ctg | gtc | act | gtt | tct | 336 |
| Ala | Arg | Arg | Met | Glu | Asp | Trp | Gly | Gln | Gly | Thr | Leu | Val | Thr | Val | Ser | |
|     |     |     | 100 |     |     |     |     | 105 |     |     |     |     | 110 |     |     | |

| gca | | | | | | | | | | | | | | | | 339 |
| Ala | | | | | | | | | | | | | | | | |

<210> SEQ ID NO 2
<211> LENGTH: 113
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Trp Met His Trp Val Ile Gln Arg Pro Gly Gln Gly Leu Glu Trp Ile
        35                  40                  45

Gly Glu Met Asn Pro Ser Asp Gly Arg Thr His Phe Asn Glu Lys Phe
    50                  55                  60

Lys Thr Lys Ala Thr Leu Thr Ile Asp Thr Ser Ser Asn Thr Ala Tyr
65                  70                  75                  80

Met Glu Leu Asn Ser Leu Thr Ser Glu Asp Ser Ala Val Tyr Tyr Cys
                85                  90                  95

Ala Arg Arg Met Glu Asp Trp Gly Gln Gly Thr Leu Val Thr Val Ser
            100                 105                 110

Ala

<210> SEQ ID NO 3
<211> LENGTH: 324
<212> TYPE: DNA

```
<213> ORGANISM: Mus musculus
<220> FEATURE:
<221> NAME/KEY: CDS
<222> LOCATION: (1)..(324)

<400> SEQUENCE: 3 gac atc aag atg acc cag tct cca tct tcc atg tat gca tct cta gga      48
Asp Ile Lys Met Thr Gln Ser Pro Ser Ser Met Tyr Ala Ser Leu Gly
1               5                   10                  15 gag aga gtc act atc act tgc aag gcg agt cag gac att aat agc tat      96
Glu Arg Val Thr Ile Thr Cys Lys Ala Ser Gln Asp Ile Asn Ser Tyr
            20                  25                  30 tta ggc tgg ttc cag cag aaa cca ggg aaa tct cct aag acc ctg ata     144
Leu Gly Trp Phe Gln Gln Lys Pro Gly Lys Ser Pro Lys Thr Leu Ile
        35                  40                  45 tat ggt gca aac aga ttg gta gat ggg gtc cca tca agg ttc agt ggc     192
Tyr Gly Ala Asn Arg Leu Val Asp Gly Val Pro Ser Arg Phe Ser Gly
    50                  55                  60 agt gga tct ggg caa gat tac tct ctc acc atc agc agc ctg gag tat     240
Ser Gly Ser Gly Gln Asp Tyr Ser Leu Thr Ile Ser Ser Leu Glu Tyr
65                  70                  75                  80 gac gat atg gga ata tat tat tgt cta cag tat gat gag ttt ccg ctc     288
Asp Asp Met Gly Ile Tyr Tyr Cys Leu Gln Tyr Asp Glu Phe Pro Leu
                85                  90                  95 acc ttc ggt gct ggg acc aag ctg gag ctg aaa cgg                     324
Thr Phe Gly Ala Gly Thr Lys Leu Glu Leu Lys Arg
            100                 105

<210> SEQ ID NO 4
<211> LENGTH: 108
<212> TYPE: PRT
<213> ORGANISM: Mus musculus

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Gly Trp Phe Gln Gln Lys Pro Gly Lys Ser Pro Lys Thr Leu Ile
        35                  40                  45

Tyr Gly Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Asp Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg
            100                 105

<210> SEQ ID NO 5
<211> LENGTH: 42
<212> TYPE: PRT
<213> ORGANISM: Homo sapiens

<400> SEQUENCE: 5

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
```

```
                35                      40

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence

<400> SEQUENCE: 6

Glu Met Asn Pro Ser Asp Gly Arg Thr His Phe Asn Glu
1               5                   10
```

MOTOR CONTROL FUNCTION IMPROVING AGENT

REFERENCE TO SEQUENCE LISTING SUBMITTED ELECTRONICALLY

The content of the electronically submitted substitute sequence listing, file name 2537_1770001_Seqlisting_ST25.txt, size 6749 bytes; and date of creation Sep. 14, 2021, filed herewith, is incorporated herein by reference in its entirety.

FIELD OF THE INVENTION

The present invention relates to a motor control function improving agent.

BACKGROUND OF THE INVENTION

Humans have an ability to control motions necessary for keeping the balance of the body by sensing the state (balance and posture) of the body through, for example, the vestibular organs and the muscles of the limbs and transmitting the stimulation to the spinal cord, cerebellum, cerebral cortex, etc. via the nerve (Non Patent Literatures 1 and 2). Such a sense of feeling a movement of the body and a change in the direction of gravity is generally called equilibrium and is regarded as one of important ability of controlling the movement.

The ability of the motor control function is decreased by aging or tiredness, and possible causes thereof are a decrease in the sensitivity of the semicircular canal or the vestibule, a decrease in the discrimination ability of sensory organs such as visual sensation, a decrease in the ability of the site of controlling the movement such as muscle and skeleton, and a decrease or disorder in the function of nerve, spinal cord, or brain.

Such a decrease in the motor control function is also a factor of many accidents including turnover accidents and fall accidents and may lead to disorders such as sprains and fractures. In addition, staggering in maintaining the standing position or moving from the standing position, staggering at the time of rising from the sitting position, and the like are increased, which may cause problems in everyday life.

Conventionally, as a method for maintaining or improving this motor control function, in particular, equilibrium, drug therapy is mainly applied. As the agent for improving a motor control function, for example, a psychosomatic nervous tranquilizing agent (such as a tranquilizer, an autonomic stabilizer, a neuropsychiatric agent, and a hypnotic sedative), a circulation improving agent (such as a vasodilator, a blood flow improving agent, a vasoconstrictor, a capillary stabilizer, a cardiovascular agent, and an arteriosclerotic agent), a metabolism improving agent (such as brain, tissue, and cell activators, and a metabolic activator), and a vitamin preparation are used (Non Patent Literature 3), but these agents are not for fundamentally treating the motor control function, and it cannot be said yet that sufficient effects are obtained. Furthermore, from the viewpoint of rehabilitation, exercise therapy is also used (Non Patent Literature 4), but exercise therapy has a difficulty in keeping motivation and a risk of injuries and is practically very difficult to perform, and a more effective method is desired.

GIP (gastric inhibitory polypeptide or glucose-dependent insulinotropic polypeptide) is a gastrointestinal hormones belonging to the glucagon/secretin family. GIP is called incretin, as with GLP-1 (glucagon-like peptide 1), and is secreted by K cells present in the small intestine upon intake of lipids or carbohydrates.

It is known that GIP promotes insulin secretion from pancreatic $\beta$ cells and enhances uptake of glucose into fat cells in the presence of insulin. Accordingly, the action of GIP is considered to be partly responsible for obesity. It has been reported that obesity is actually suppressed by inhibiting the function of GIP (Non Patent Literature 5).

Furthermore, it has been reported that GIP is partly responsible for insulin resistance (Non Patent Literature 1). When insulin resistance occurs, glucose-absorbing effect mediated by insulin is reduced, as a result, causing hyperinsulinemia. Hyperinsulinemia is recognized to be a primary cause leading to occurrence of various lifestyle-related diseases including obesity, and prevention and improvement of insulin resistance are important also from the aspect of reducing the risk of lifestyle-related diseases.

However, there is no report that GIP has a relation with a motor control function, and it is not known at all that a motor control function can be improved by suppressing the GIP function.

[Non Patent Literature 1]
Haruo Sugi, et al., "(Zintai Kinou Seirigaku (Physiology of Human Body Functions), 5th revision", Nanzando, 2010
[Non Patent Literature 2]
Motohiro Kato, "Heiko-shogai no Kizyo to Kanbetsu (Mechanism and Discrimination of Dysequilibrium," Jibi to Rinsho, 32:1097-1102, 1986
[Non Patent Literature 3]
Takashi Matsunaga, "Memai ni taisuru Yakubutsu Ryoho no Sentaku to Koka (Selection and effect of drug therapy on dizziness)", Jibi Rinsho, 65 (Special issue 1): 653-671, 1972
[Non Patent Literature 4]
Yasushi Uchiyama and Koji Tokumasu, "Zenteimeiro-sei Sikkan ni tomonau Memai/Heiko shogai Kanja no Undo Ryoho (Exercise therapy of dizziness and dysequilibrium patients due to vestibular labyrinthine disease)", Equilibrium Research. 50(2): 199-205, 1991
[Non Patent Literature 5]
Miyawaki K, et al., Nat. Med. 8(7): 738-42, 2002

SUMMARY OF THE INVENTION

The present invention relates to the following aspects 1) to 6):

1) a motor control function improving agent comprising a GIP function inhibitor as an active ingredient;
2) use of a GIP function inhibitor for producing a motor control function improving agent;
3) a GIP function inhibitor for use in improvement of a motor control function;
4) use of a GIP function inhibitor for improving a motor control function;
5) a method for improving a motor control function, comprising administering a GIP function inhibitor to a subject in need thereof; and
6) a method for evaluating or selecting a motor control function improving agent, comprising the following steps:
(I) measuring GIP function inhibitory activity of test substances;
(II) evaluating the GIP function inhibitory activity of the test substances based on the results of (I); and (III) evaluating or selecting a test substance that increases or enhances GIP function inhibitory activity as a motor control function improving agent.

DESCRIPTION OF EMBODIMENTS

Figure 1:
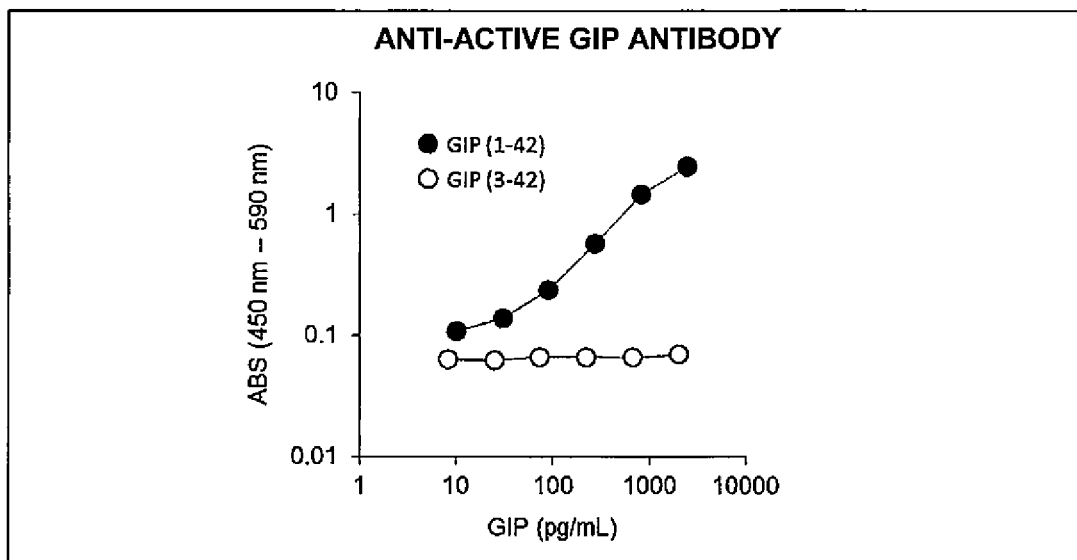
FIG. 1 is a calibration curve for a sandwich ELISA using an anti-active GIP antibody.

The present invention relates to provide a motor control function improving agent that improves a motor control function decreased by aging or tiredness and a method for evaluating or selecting the motor control function improving agent.

The present inventors examined the relationship between GIP and motor control function and found that motor control function is significantly decreased by administration of GIP, the motor control function can be improved by suppressing the GIP function, and a motor control function improving agent can be screened by evaluating the GIP function inhibitory activity.

The motor control function improving agent of the present invention shows an effect of improving a motor control function, for example, a motor control function decreased by aging or tiredness. Accordingly, the agent is useful for, for example, a decrease in the sensitivity of the semicircular canal and the vestibule, a decrease in the discrimination ability of sensory organs such as visual sensation, a decrease in the ability of the site of controlling the movement such as muscle and skeleton, and a decrease or disorder in the function of nerve, spinal cord, or brain.

In the present invention, GIP (gastric inhibitory polypeptide or glucose-dependent insulinotropic polypeptide) is a polypeptide consisting of 42 amino acids. GIP(1-42) has physiological activity (active GIP), but becomes inactive GIP(3-42) by cleavage of two amino acids at the N-terminus with dipeptidyl peptidase-4 (DPP-4) present in vivo.

In the present invention, the "GIP function inhibitor" means a substance that inhibits or suppresses the function of GIP as a gastrointestinal hormone, i.e., a substance that inhibits the function at the GIP gene or GIP receptor gene level or at the GIP itself or GIP receptor level. Specifically, the inhibitor is, for example, an anti-GIP antibody, a GIP receptor antagonist, or a GIP secretion- or increase-suppressing agent.

In the present invention, the "anti-GIP antibody" may be any antibody that at least inhibits the function of active GIP and may be a polyclonal antibody or a monoclonal antibody and preferably an antibody that substantially does not bind to inactive GIP (referred to as "anti-active GIP antibody") described in WO 2016/104439 and JP-A-2013-138638. The binding constant (Ka) with active GIP is preferably $10^7 \, M^{-1}$ or more, more preferably $10^8 \, M^{-1}$ or more, even more preferably $10^9 \, M^{-1}$ or more.

The anti-active GIP antibody includes antibodies in which the amount of a test antibody bound to inactive GIP is 10% or less at most, preferably 5% or less, more preferably 1% or less, even more preferably 0.1% when the amount of the test antibody bound to active GIP is assumed to be 100%. The amount of the test antibody bound to active or inactive GIP can be determined by measuring the binding between the test antibody and active or inactive GIP through a method such as western blotting, immunoprecipitation, immunohistochemical staining, or ELISA.

The anti-active GIP antibody is, for example, an antibody recognizing the 8th and subsequent amino acids from the N-terminus of active GIP (SEQ ID NO: 5) and is preferably an antibody recognizing one or more amino acids selected from at least the 8th to 10th amino acids (SDY).

The anti-active GIP antibody is preferably an antibody further including a region consisting of the amino acid sequence represented by the following formula (1) or a conservative sequence modification thereof in an H-chain:
EMNPSDGRTHFNE (1) (SEQ ID NO:6).

The alphabetical letters in formula (1) mean the one-letter codes of amino acids, and the sequence is shown in order from the N-terminus to the C-terminus. Here, F is phenylalanine, T is threonine, D is aspartic acid, E is glutamic acid, M is methionine, N is asparagine, P is proline, S is serine, G is glycine, R is arginine, and H is histidine.

In the present specification, the "conservative sequence modification" is an amino acid modification in a region other than the complementarity determining region (CDR) participating in antigen determination, and means amino acid modification that does not significantly affect or change the reactivity of the antibody consisting of the unmodified amino acid sequence. Such conservative sequence modification encompasses substitution, addition, and deletion of one to several, preferably 1 to 3, more preferably one amino acid. The conservatively modified amino acid sequence has, for example, a sequence identity of 90% or more, preferably 95% or more, more preferably 99% or more with the unmodified amino acid sequence. The modification can be introduced into the antibody of the present invention by a standard technique known in the art, such as site-directed mutagenesis or PCR-mediated mutagenesis. Examples of the conservative amino acid substitution include substitution of an amino acid residue with an amino acid residue having a similar side chain (a family of the amino acid residue). Such families of amino acid residues are defined in the art and include amino acids having basic side chains (e.g., lysine, arginine, and histidine), acid side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine, isoleucine, proline, phenylalanine, and methionine), β-branched side chains (e.g., threonine, valine, and isoleucine), and aromatic side chains (e.g., tyrosine, phenylalanine, tryptophan, and histidine).

The identity between amino acid sequences refers to the ratio (%) of the number of positions at which the identical amino acid residues are present in both sequences relative to the number of full-length amino acid residues when the two amino acid sequences are aligned. Specifically, for example, the identity can be calculated by the Lipman-Pearson method (Science, 227, 1435, (1985)) and determined by analysis using a homology analysis (Search homology) program of genetic information processing software Genetyx-Win (Ver.5.1.1; Software Development) with setting Unit size to compare (ktup) at 2.

The amino acid sequence represented by formula (1) described above encodes the region consisting of 13 amino acid residues at the 50th to 62nd positions of the amino acid sequence represented by SEQ ID NO: 2 representing the H-chain variable region.

Accordingly, the anti-active GIP antibody more preferably includes a region consisting of the amino acid sequence represented by SEQ ID NO: 2 or a conservative sequence modification thereof as the H-chain variable region. Furthermore, the anti-active GIP antibody more preferably includes a region consisting of the amino acid sequence represented by SEQ ID NO: 2 or a conservative sequence modification thereof as the H-chain variable region and a region consisting of the amino acid sequence represented by SEQ ID: 4 or a conservative sequence modification thereof as the L-chain variable region.

Examples of the anti-active GIP antibody including a region consisting of the amino acid sequence represented by SEQ ID NO: 2 as the H-chain variable region and a region consisting of the amino acid sequence represented by SEQ ID NO: 4 as the L-chain variable region include the monoclonal antibody produced by hybridoma 9B9H5-B9 line shown in Production Example 1 described later.

The anti-GIP antibody of the present invention may be a fragment of the antibody such as F(ab')$_2$, F(ab'), single chain Fv (scFv), disulfide-linked Fv (dsFv) in which amino acid residues substituted for the cysteine residues in the VH and the VL are linked to each other through a disulfide bond, or a polymer thereof, or a dimerized V region (Diabody) in which scFv is dimerized as long as the fragment has the reactivity. Furthermore, the fragment of the antibody may be a peptide including a part of the anti-active GIP antibody, as long as the peptide has the reactivity, and specifically includes a peptide including a part of the amino acid sequence constituting the antibody and having the reactivity.

In addition, the immunoglobulin class of the anti-GIP antibody of the present invention is not particularly limited and may be any of IgG, IgM, IgA, IgE, IgD, and IgY immunoglobulin classes and is preferably IgG. The antibody of the present invention encompasses antibodies of any isotype.

In addition, the anti-GIP antibody of the present invention may be any one of antibodies of non-human animals, human chimeric antibodies, humanized antibodies, and human antibodies. Examples of the antibodies of non-human animals include antibodies of mouse, rat, hamster, and guinea pig, and mouse antibodies are preferred.

Here, the "human chimeric antibody" is an antibody modified by genetic engineering such that the constant region of an antibody derived from a non-human animal and specifically binding to GIP is replaced with the corresponding constant region of a human antibody, and is preferably a human-mouse chimeric antibody. The "humanized antibody" is an antibody modified by genetic engineering such that the primary structure except for the H chain and L chain complementarity determining region (CDR) of an antibody derived from a non-human animal and specifically binding to GIP is replaced with the corresponding primary structure of a human antibody. The "human antibody" means a human antibody that is an expression product of a completely human-derived antibody gene.

The anti-GIP antibody that can be used is a monoclonal antibody produced by a known method, in addition to a commercially available polyclonal antibody (Bioss Inc.). Examples of the monoclonal antibody derived from a mammal include those produced by hybridomas and those produced by a well-known genetic engineering technique using a designed antibody gene or antibody fragment gene.

For example, the anti-active GIP antibody described above is produced as a recombinant single-chain antibody protein (scFv) having antigen binding ability by inserting a DNA encoding an H-chain variable region (e.g., a DNA consisting of the nucleotide sequence represented by SEQ ID NO: 1) and a DNA encoding an L-chain variable region (e.g., a DNA consisting of the nucleotide sequence represented by SEQ ID NO: 3) into the downstream of a promoter in respective appropriate vectors to construct recombinant vectors, introducing the recombinant vectors into host cells to produce an H-chain and an L-chain from the resultant transformants, and linking the chains via a possible peptide; or by linking a DNA encoding an H-chain variable region (e.g., a DNA consisting of the nucleotide sequence represented by SEQ ID NO: 1) and a DNA encoding an L-chain variable region (e.g., a DNA consisting of the nucleotide sequence represented by SEQ ID NO: 3) via a DNA encoding a known linker, inserting the resultant DNA construct into the downstream of a promoter in an appropriate vector to construct a recombinant vector and expressing the DNA sequence in a host cell (see, for example, MacCfferty, J., et al., Nature, 348, 552-554, 1990; and Tim Clackson, et al., Nature, 352, 642-628, 1991). Furthermore, the anti-active GIP antibody may be produced by linking a DNA encoding a variable region and a DNA encoding a constant region and expressing the DNA sequence. In this case, the constant region and the variable region may be derived from the same antibody or may be derived from a different antibody.

As described above, an amino acid mutation for preparing functionally equivalent polypeptides can be introduced by, for example, site-directed mutagenesis.

An anti-active GIP antibody-producing hybridoma can be basically produced by a known technique as follows.

For example, active GIP or a peptide including an N-terminal amino acid sequence (a peptide consisting of the 1st to 15th amino acids of SEQ ID NO: 5) is linked to an appropriate carrier protein, for example, keyhole limpet hemocyanin (KLH) or bovine serum albumin, as needed, to enhance the immunogenicity and is used for immunization of a non-human mammal to produce the hybridoma. The active GIP or the peptide used as the sensitizing antigen (immunogen) can be produced by genetic engineering or chemical synthesis.

The mammal to be immunized with the sensitizing antigen is not particularly limited, is preferably selected considering the compatibility with myeloma cells of a mammal as a parent cell to be used for cell fusion and is usually a rodent such as a mouse, a rat, or a hamster.

An animal is immunized with the sensitizing antigen according to a known method. For example, the sensitizing antigen is injected intraperitoneally or subcutaneously into a mammal for immunization. Specifically, the sensitizing antigen is diluted or suspended in, for example, PBS (phosphate-buffered saline) or physiological saline to obtain an appropriate amount, the dilution or suspension is, if desired, mixed with an appropriate amount of a common adjuvant, for example, Freund's complete adjuvant for emulsification. The emulsion is then administered subcutaneously, intradermally, or intraperitoneally to an animal for temporal stimulation, and the same procedure is repeated as needed. The amount of the antigen administered is appropriately determined according to the administration route and the animal species and, usually, is preferably about from 10 µg to 1 mg per once. After confirmation of an increase in the level of the desired antibody in the serum of the animal thus immunized, the immunocytes are taken from the mammal having an increased antibody level and are used for cell fusion. In particular, examples of the immunocyte preferred for the cell fusion include a spleen cell.

As myeloma cells of the mammal serving as the other parent cell to be fused with the immunocytes, various known cell lines, such as P3X63, NS-1, MPC-11, and SP2/0, are appropriately used.

The immunocytes and the myeloma cells can be fused according to a known method, for example, a Kohler's method (Kohler, et al., Nature, vol. 256, p 495-497 (1975)). That is, the immunocytes and the myeloma cells are mixed in the presence of a cell fusion promoter, such as polyethylene glycol (PEG having an average molecular weight of 1,000 to 6,000, concentration: 30% to 60%) or hemagglutinating virus of Japan (HVJ) in a nutrient medium, such as a RPMI1640 medium or a MEM medium, containing an auxiliary, such as dimethyl sulfoxide, if desired, to form fused cells (hybridomas).

The hybridomas formed by fusion are cultured in a selection medium, such as a medium containing hypoxanthine, thymidine, and aminopterin (HAT medium), for 1 to 7 days and thereby separated from unfused cells. The resulting hybridomas are subjected to further selection based on a produced antibody (antibody binding to active GIP and not substantially binding to inactive GIP).

The selected hybridomas are cloned according to a known limiting dilution method to establish a monoclonal antibody-producing hybridoma.

A method for detecting the activity of the antibody produced by the hybridoma can be a known method, such as an ELISA, agglutination, or radioimmunoassay.

In order to obtain a monoclonal antibody from the resulting hybridoma, for example, the following methods are adopted: a method which involves culturing the hybridoma according to an ordinary method to obtain the monoclonal antibody as a culture supernatant, or a method which involves administering the hybridoma to a mammal compatible therewith, proliferating the hybridoma, and obtaining the monoclonal antibody as an ascitic fluid thereof.

The antibody can be purified by a known purification method, such as a salting-out method, a gel filtration method, ion exchange chromatography, or affinity chromatography.

In the present invention, examples of the "GIP receptor antagonist" include methylidene hydrazide compounds described in WO 2003/097031, specifically, 4-hydroxybenzoic acid (2-bromobenzylidene) hydrazide, 3-cyano-4-hydroxybenzoic acid [1-(2,3,5,6-tetramethylbenzyl)indol-4-yl]methylidene hydrazide, 3-chloro-4-hydroxybenzoic acid (4-methoxynaphthalen-1-yl)methylidene hydrazide, and 3-chloro-4-hydroxybenzoic acid [1-(5-chlorothiophen-2-ylmethyl)-1H-indol-5-yl]methylidene hydrazide.

In the present invention, examples of the "GIP secretion- or increase-suppressing agent" include BMPP (3-bromo-5-methyl-2-phenylpyrazolo[1,5-a]pyrimidin-7-ol) (WO 2001/87341), alginic acid (JP-A-2013-166741), phosphatidylethanolamine (JP-A-2010-222284), polyglutamic acid (JP-A-2012-144486), quillaja (JP-A-2012-171914), lysophosphatidylinositol (JP-A-2012-171915), cellulose nanofiber (JP-A-2009-126837), β-chitin nanofiber (JP-A-2010-241713), diacylglycerol (JP-A-2006-342084), hydroxypropylated starch (JP-A-2006-342085), monoacylglycerol (JP-A-2007-290989), a very long chain fatty acid having 20 or more carbon atoms (for example, arachidic acid, behenic acid, lignoceric acid, cerotic acid, montanic acid, melissic acid, lacceric acid, gadoleic acid, dihomo-γ-linolenic acid, arachidonic acid, eicosapentaenoic acid, erucic acid, docosapentaenoic acid, docosahexaenoic acid, nervonic acid, hexacosenoic acid, and octacosenoic acid: JP-A-2011-225458), triacylglycerol containing 1 mass % or more docosahexaenoic acid and 1 mass % or more of eicosapentaenoic acid as constituent fatty acids (JP-A-2013-063937), long chain unsaturated fatty acid ethanolamide (for example, oleylethanolamide, linoleylethanolamide, linolenylethanolamide, homo-γ-linolenylethanolamide, arachidonylethanolamide, and 7,10,13,16-docosatetraenylethanolamide: JP-A-2010-180203), a rice bran extract (JP-A-2012-515139), triacylglycerol containing 10 mass % or more α-linolenic acid as a constituent fatty acid (JP-A-2013-075887), acylglycerol with a C14 to C18 saturated fatty acid bound at the 2-position of the glycerol skeleton (for example, 2-acylmonoglycerol with lauric acid (12:0), myristic acid (14:0), palmitic acid (16:0), linoleic acid (18:2), oleic acid (18:1), stearic acid (18:0), or arachidonic acid (20:4) bound at the 2-position: JP-A-2016-047805), a squeeze or extract of common mushroom (*Agaricus bisporus*) (PCT/JP2017/043101), and wheat bran (Japanese Patent Application No. 2016-234973).

As shown in Examples described later, the anti-GIP antibody suppresses a decrease in the motor control function caused by administration of GIP and thus has an activity of improving the motor control function of aged mice.

Accordingly, a GIP function inhibitor such as the anti-GIP antibody can be a motor control function improving agent and can be used for producing a motor control function improving agent.

In addition, the GIP function inhibitor can be used for improving a motor control function. Here, the use can be use for a human being or a non-human animal or in a sample derived therefrom, and may be therapeutic use or non-therapeutic use. The term "non-therapeutic" is a concept that does not include medical practice, i.e., a concept not including a method for operation, treatment, or diagnosis for a human being, more specifically, a concept not including a method for performing operation, treatment, or diagnosis for a human being by a doctor or a person instructed by a doctor.

In the present invention, the "motor control function" means a function of controlling the motion involved in, for example, equilibrium, balance ability, and agility, and the "improvement in motor control function" means enhancement of the function of controlling the motion involved in, for example, equilibrium, balance ability, and agility.

The motor control function improving agent of the present invention can be human or veterinary medicine showing an effect of improving the motor control function or a material or preparation to be used by being blended in medicine.

When the motor control function improving agent of the present invention is used as medicine, the medicine can be administered in an arbitrary dosage form. Examples of the dosage form include oral administration in the form of, for example, tablets, capsules, granules, powders, and syrups, and parenteral administration in the form of, for example, injections, suppositories, inhalants, transdermal absorbents, and external preparations. Preferred form is parenteral administration.

The medicinal preparations of such various dosage forms can be prepared from the GIP function inhibitor of the present invention alone or in appropriate combination with other pharmaceutically acceptable ingredients, such as an excipient, a binder, a filler, a disintegrant, a surfactant, a lubricant, a dispersant, a buffering agent, a preservative, a corrective agent, a flavor, a coating agent, a carrier, and a diluent.

The content of the GIP function inhibitor in the motor control function improving agent of the present invention is preferably 0.001 mass % or more, more preferably 0.01 mass % or more; preferably 10 mass % or less, more preferably 5 mass % or less, even more preferably 1 mass % or less, even more preferably 0.1 mass % or less; and is preferably from 0.001 to 10 mass %, more preferably from 0.001 to 5 mass %, even more preferably from 0.001 to 1 mass %, even more preferably from 0.01 to 0.1 mass %.

The amount of the motor control function improving agent of the present invention administered or taken can vary depending on the condition, weight, sex, age, or other factors of the subject. In the case of oral administration or intake, the amount as the GIP function inhibitor is preferably 1 mg or more, more preferably 5 mg or more; and preferably 500 mg or less, more preferably 100 mg or less, even more preferably 20 mg or less per day for an adult.

The subject to be administered with the motor control function improving agent of the present invention is preferably a human suffering from a locomotive syndrome which is a high risk of becoming in need of nursing care by motility disturbance.

The method for evaluating or selecting the motor control function improving agent of the present invention includes a step (I) of measuring GIP function inhibitory activity of test substances, a step (II) of evaluating the GIP function inhibitory activity of the test substances based on the results of the step (I), and a step (III) of evaluating or selecting a test substance that increases or enhances GIP function inhibitory activity as a motor control function improving agent.

Here, examples of the method for measuring GIP function inhibitory activity include the following methods.

1) GIP receptor cDNA is introduced into GIP receptor-expressing cells, and cAMP is produced by GIP using the cells in the presence of a test substance. Subsequently, the cAMP is extracted and is measured by immunoassay.

2) GIP receptor cDNA is introduced into GIP receptor-expressing cells, and a gene including a bacterial lac Z gene linked to a cAMP-dependent promoter is introduced into the cells. The cells are reacted with GIP in the presence of a test substance. The activity of β-galactosidase accumulated in the cells according to the cAMP produced by the GIP activity is measured.

3) GIP receptor cDNA is introduced into GIP receptor-expressing cells, and a test substance and a radiolabeled GIP are added to the cells. After incubation, the radioactivity is measured.

4) Intestine-derived or neuron-derived cells producing GIP are stimulated with a test substance, and then GIP produced in the cells or culture supernatant is quantitatively measured.

5) The amount of GIP secreted in the presence of a test substance by nutrients, such as lipids and carbohydrates, is measured by ELISA.

Evaluation of the GIP function inhibitory activity of test substances is performed by identifying a test substance that increases or enhances the GIP function inhibitory activity.

For example, the evaluation can be performed by comparing the GIP function inhibitory activities measured when test substances are added at different concentrations. In a more specific example, the GIP function inhibitory activities are compared between a higher concentration of test substance addition group and a lower concentration of test substance addition group; between a test substance addition group and a placebo addition group; or between before and after the addition of a test substance. When the GIP function inhibitory activity is increased or enhanced by addition of a test substance or by addition of a higher concentration of a test substance, the test substance can be identified as a substance that increases or enhances the GIP function inhibitory activity.

The test substance identified as one that increases or enhances the GIP function inhibitory activity is evaluated or selected as a motor control function improving agent.

The test substance is not particularly limited as long as the test substance is a substance that is desired to be used for improving a motor control function, may be a naturally occurring substance or be a substance artificially synthesized by a chemical or biological method, and may be a compound, composition, or mixture.

Regarding the above-described embodiments, in the present invention, the following aspects are further disclosed.

<1> A motor control function improving agent comprising a GIP function inhibitor as an active ingredient.

<2> Use of a GIP function inhibitor for producing a motor control function improving agent.

<3> A GIP function inhibitor for use in improvement of a motor control function.

<4> (Non-therapeutic) use of a GIP function inhibitor for improving a motor control function.

<5> A method for improving a motor control function, comprising administering a GIP function inhibitor to a subject in need thereof.

<6> In aspects <1> to <5>, the GIP function inhibitor is an anti-GIP antibody, a GIP receptor antagonist, or a GIP secretion- or increase-suppressing agent.

<7> In aspect <6>, the anti-GIP antibody is preferably an anti-active GIP antibody.

<8> In aspect <6>, the GIP receptor antagonist is preferably 4-hydroxybenzoic acid (2-bromobenzylidene) hydrazide, 3-cyano-4-hydroxybenzoic acid [1-(2,3,5,6-tetramethylbenzyl) indol-4-yl]methylidene hydrazide, 3-chloro-4-hydroxybenzoic acid (4-methoxynaphthalen-1-yl)methylidene hydrazide, or 3-chloro-4-hydroxybenzoic acid [1-(5-chlorothiophen-2-ylmethyl)-1H-indol-5-yl]methylidene hydrazide.

<9> In aspect <6>, the GIP secretion- or increase-suppressing agent is preferably a squeeze or extract of common mushroom, wheat bran, 3-bromo-5-methyl-2-phenylpyrazolo[1,5-a]pyrimidin-7-ol, alginic acid, phosphatidylethanolamine, polyglutamic acid, quillaja, lysophosphatidylinositol, cellulose nanofiber, β-chitin nanofiber, diacylglycerol, hydroxypropylated starch, monoacylglycerol, a very long chain fatty acid having 20 or more carbon atoms, triacylglycerol containing 1 mass % or more of docosahexaenoic acid and 1 mass % or more of eicosapentaenoic acid as constituent fatty acids, long chain unsaturated fatty acid ethanolamide, a rice bran extract, triacylglycerol containing 10 mass % or more of α-linolenic acid as a constituent fatty acid, or acylglycerol with a C14 to C18 saturated fatty acid bound at the 2-position of the glycerol skeleton.

<10> In aspect <7>, the anti-active GIP antibody is preferably an anti-active GIP antibody that binds to active GIP and does not substantially bind to inactive GIP, wherein the antibody at least recognizes one or more amino acids selected from the 8th to 10th amino acids of the amino acid sequence represented by SEQ ID NO: 5, and includes a region consisting of the amino acid sequence represented by the following formula (1) or a conservative sequence modification thereof in an H-chain:

EMNPSDGRTHFNE (1) SEQ ID NO:6.

<11> In aspect <10>, the anti-active GIP antibody is preferably an antibody including a region consisting of the amino acid sequence represented by SEQ ID NO: 2 or a conservative sequence modification thereof as an H-chain variable region.

<12> In aspect <11>, in the anti-active GIP antibody, the conservatively modified amino acid sequence preferably has an identity of 90% or more with the amino acid sequence represented by SEQ ID NO: 2.

<13> In aspect <10>, the anti-active GIP antibody is preferably an antibody including a region consisting of the amino acid sequence represented by SEQ ID NO: 2 or a conservative sequence modification thereof as an H-chain variable region and including a region consisting of the amino acid sequence represented by SEQ ID NO: 4 or a conservative sequence modification as an L-chain variable region.

<14> In aspect <13>, in the anti-active GIP antibody, the amino acid sequence obtained by conservative sequence modification of the amino acid sequence represented by SEQ ID NO: 2 has an identity of 90% or more with the amino acid sequence represented by SEQ ID NO: 2, and the amino acid sequence obtained by the conservative sequence modification of the amino acid sequence represented by SEQ ID NO: 4 has an identity of 90% or more with the amino acid sequence represented by SEQ ID NO: 4.

<15> A method for evaluating or selecting a motor control function improving agent, comprising the following steps:

(I) measuring GIP function inhibitory activity of test substances;

(II) evaluating the GIP function inhibitory activity of the test substances based on the results of the step (I); and (III) evaluating or selecting a test substance that increases or enhances GIP function inhibitory activity as a motor control function improving agent.

<16> The method according to aspect <15>, wherein the GIP function inhibitory activity is measured by introducing GIP receptor cDNA into GIP receptor-expressing cells, producing cAMP by GIP using the cells in the presence of a test substance, subsequently extracting the cAMP, and measuring the cAMP by immunoassay.

EXAMPLES

Production Example 1: Preparation of Anti-Active GIP Antibody (1) Synthesis of Peptide for Immunization Polyethylene glycol was added to N-terminus 15 amino acids of active GIP (GIP(1-15)) (PEGylation (polyethylene glycolation)), and keyhole limpet hemocyanin (KLH) was then chemically bonded thereto to produce KLH-linked PEGylated GIP (1-15) as an immunogen. PEGylated N-terminus 15 amino acids of active GIP (GIP(1-15)) was used as an antigen (1) for measurement, and PEGylated N-terminus 13 amino acids of inactive GIP (GIP(3-15)) was used as an antigen (2) for measurement.

(2) Immunization

BALB/c mice (Oriental Yeast Co., Ltd.) were immunized subcutaneously in the back. In the first immunization, an emulsion prepared by mixing the antigen prepared as above and Freund's complete adjuvant was administered. Booster immunization was performed with an emulsion prepared by mixing the antigen and Freund's incomplete adjuvant every two weeks from the first immunization. The amount of the antigen used in one immunization was in a range of 0.1 to 0.2 mg. Seven weeks after the first immunization, the antibody titer of the serum collected from each mouse was measured to confirm an increase in the antibody titer.

(3) Cell Fusion

The spleen was excised from the mouse with an increased antibody titer to obtain spleen cells. The obtained spleen cells were fused with mouse myeloma cell line P3U1 by a PEG method. Subsequently, the fused cells were seeded in 20 96-well plates ($1\times10^5$ cells/well).

(4) Screening

The reaction between the hybridoma culture supernatant and the antigen (1) and (2) for measurement was evaluated by ELISA using immobilized antigen (1) and (2), and hybridomas that are positive for the antigen (1) and negative for the antigen (2) were selected as anti-active GIP monoclonal antibody-producing hybridomas.

(5) Cloning

Antibody-producing hybridoma was cloned by culturing the hybridomas obtained above through a limiting dilution method to obtain single colonies, and single colony-forming wells were subjected to ELISA again to establish 9B9H5-B9 line, which produces an antibody that is positive for the antigen (1) and negative for the antigen (2) (WO 2016/104439).

To preserve the resulting antibody-producing hybridomas, the hybridomas were cultured and collected in the logarithmic growth phase and were then prepared to a cell concentration of $1\times10^6$ cells/mL with a cryopreservation liquid-containing FBS (fetal bovine serum). The hybridomas were then dispensed into cryogenic tubes at $1\times10^6$ cells/tube and were preserved at $-80°$ C. in a Bicell.

(6) Antibody Production

The resulting antibody-producing hybridomas in the cryogenic vial were initiated in a hybridoma-SFM (Serum-Free Medium). After amplifying and culturing the hybridomas, culturing was performed in two roller bottles (500 mL×2, 1 L), and the culture supernatant was collected. The collected culture supernatant was purified to a monoclonal antibody by affinity chromatography using Protein A.

Test Example 1: Reactivity with Active GIP by ELISA

The reactivity between the monoclonal antibody prepared in Production Example 1 and active GIP was confirmed by ELISA. The amino group of the anti-active GIP monoclonal antibody was biotinylated with NH2 group biotinylation kit (manufactured by Dojindo Laboratories). ELISA was performed using the produced biotinylated anti-active GIP monoclonal antibody at 1 µg/mL instead of a detection antibody, GIP detection antibody (biotinylated anti-total GIP monoclonal antibody), included in Human (total) GIP ELISA kit (manufactured by EMD Millipore Corporation). A 4-fold dilution series of GIP(1-42) or GIP(3-42) was prepared in 6 steps (8.2 to 2000 pg/mL) with a 2000 pg/mL solution as the highest concentration. By using an anti-total GIP monoclonal antibody (included in Human GIP (total) ELISA kit manufactured by EMD Millipore Corporation) as a capture antibody, the biotinylated anti-active GIP monoclonal antibody as a detection antibody, and a peroxidase-streptavidin conjugate for detection, sandwich ELISA was conducted to prepare a calibration curve with GIP concentration on the X-axis and 450 nm-590 nm absorbance on the Y-axis (FIG. 1).

As shown in FIG. 1, the absorbance was not increased in GIP(3-42) even in a high-concentration range, and the absorbance was increased only in GIP(1-42) in a concentration-dependent manner. Accordingly, it was verified that the monoclonal antibody prepared in Production Example 1 is an antibody which does not show cross-reactivity with GIP(3-42) and be capable of specifically detecting GIP(1-42).

Example 1: Decrease in Motor Control Function by GIP and Suppression of Decrease in Motor Control Function by Anti-GIP Antibody (1) Animal and Breeding Method Six-week-old leptin receptor deficient C57BLKS/J male mice (db/db mice, Oriental Yeast Co., Ltd.) were transferred (room temperature: 23° C., humidity: 55±10%, light period: 7:00 to 19:00) and were fed with food and water ad libitum. The food was CE-2 (CLEA Japan, Inc.), and the mice were acclimated for 2 weeks under the above-mentioned environment and were then used for testing.

(2) Preparation of GIP Solution and GIP-Binding Anti-GIP Antibody Solution by Antigen Antibody Reaction Mouse-derived GIP (manufactured by AnaSpec, Inc.) was dissolved in physiological saline at a concentration of 500 nM to give a GIP solution. Mouse-derived GIP (manufactured by AnaSpec, Inc.) and the anti-active GIP antibody produced in Production Example 1 were dissolved in physiological saline at concentrations of 500 nM and 0.1 mg/mL, respectively, and the resulting solution was incubated for 1 to 2 hours at room temperature to give a GIP-binding anti-GIP antibody solution.

(3) Administration Amount and Administration Method

Physiological saline (control group), the GIP solution (5 nmol/kg body weight). (GIP administration group), or the GIP-binding anti-GIP antibody solution (GIP: 5 nmol/kg body weight, anti-GIP antibody: 1 mg/kg body weight) (GIP+anti-GIP antibody administration group) was intraperitoneally administered to mice (8-week-old) every morning (9:00 to 10:00 a.m.). After administration for 28 days, the motor control function was measured by a rotarod test.

(4) Rotarod (Motor Control Function) Test

The motor control function (the accommodation ability reflecting balance ability and agility) was evaluated by measuring the capacity of staying on a rod rotating at various speeds using a rotarod (MK-600A, manufactured by Muromachi Kikai Co., Ltd.). Each mouse was placed on a stationary rod, and the number of times of falling was measured with a program of 6 rpm (1 min)→12 rpm (1 min)→16 rpm (1 min)→20 rpm (1 min)→24 rpm (1 min)→28 rpm (1 min).

(5) Statistical Analysis

The analysis results were shown as the average value (Ave.)±standard error (SE). The statistical analysis was performed using 2-way ANOVA followed by Bonferroni's post hoc test, and the difference was judged to be statistically significant when the P value was 0.05 or less.

(6) Results

Figure 2:
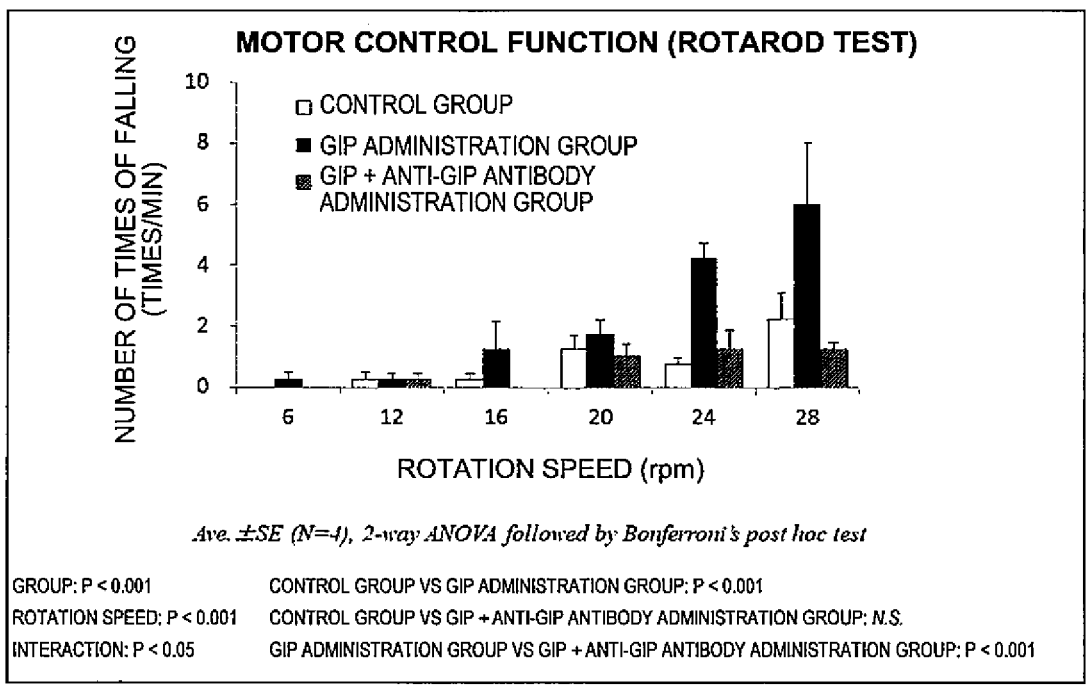
FIG. 2 is a graph showing changes in the motor control function by continuous administration of GIP or a GIP-binding anti-GIP antibody.

A significant decrease in the motor control function (an increase in the number of times of falling with an increase of the rotation speed) was observed in the GIP administration group compared to the control group. In the GIP+anti-GIP antibody administration group, a decrease in the motor control function was not observed, while observed in the GIP administration group, and the motor control function was equivalent to that of the control group (FIG. 2).

Example 2: Age-Related Change of Blood GIP Level (1) Animal and Breeding Method Four-week-old C57BL/6J male mice (CLEA Japan, Inc.) were transferred (room temperature: 23° C., humidity: 55±10%, light period: 7:00 to 19:00) and were fed with food and water ad libitum. The mice were acclimated using CE-2 (CLEA Japan, Inc.) as food for 1 week and were then fed with normal diet (D12450K, Research Diets, Inc.) or high fat diet (D12451, Research Diets, Inc.) for 95 weeks.

(2) Blood Collection

Whole blood of each week old mouse (5-, 10-, 15-, 20-, 30-, 40-, 50-, 65-, 80-, and 100-week-old mice) was collected from the abdominal vena cava under isoflurane anesthesia.

(3) Measurement of Blood GIP Level

The collected blood was centrifuged to prepare each plasma fraction, and the blood GIP concentration was then measured according to a usual method with a GIP ELISA kit (manufactured by EMD Millipore Corporation) as the total GIP.

(4) Statistical Analysis

The analysis results were shown as the average value (Ave.)±standard error (SE). The statistical analysis was performed using 2-way ANOVA followed by Bonferroni's post hoc test, and the difference was judged to be statistically significant when the P value was 0.05 or less.

(5) Results

Figure 3:
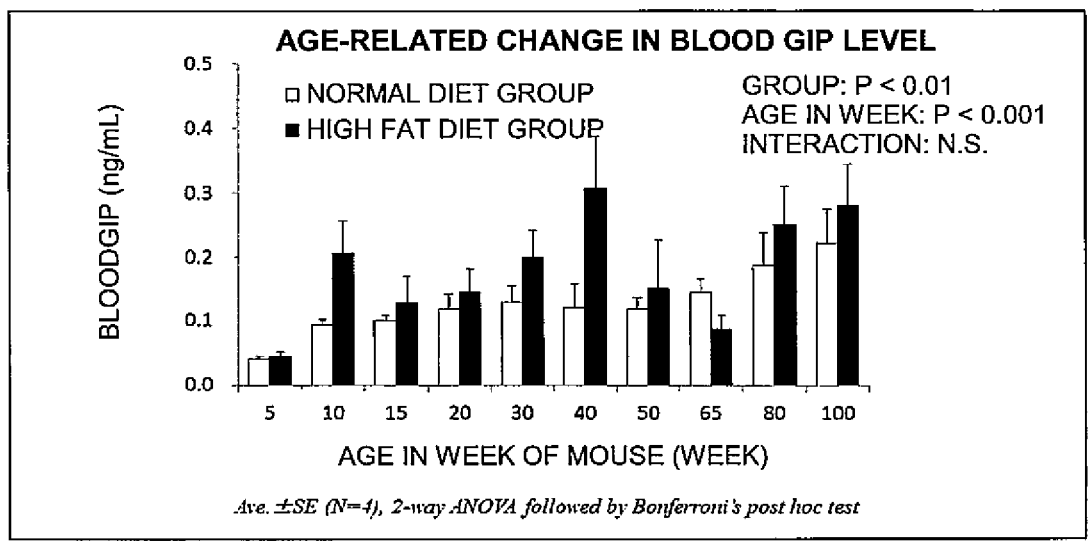
FIG. 3 is a graph showing age-related changes in the blood GIP level.

An increase in the blood GIP concentration with aging was observed. In particular, a significant increase in the blood GIP level was observed in the high fat diet group compared to the normal diet group (FIG. 3). Since it is known that the total GIP and the amount of active GIP change in conjunction (WO 2012-121302), it is considered that the amount of active GIP is also increased.

Example 3: Motor Control Function Improving Activity of Anti-GIP Antibody on Aged Mouse (1) Animal and Breeding Method Four-week-old C57BL/6J male mice (CLEA Japan, Inc.) were transferred (room temperature: 23° C., humidity: 55±10%, light period: 7:00 to 19:00) and were fed with food (D12450K, Research Diets, Inc.) and water ad libitum for 111 weeks.

(2) Preparation of Anti-GIP Antibody Solution

The anti-active GIP antibody produced in Production Example 1 was dissolved in physiological saline at a concentration of 0.05 mg/mL to give an anti-GIP antibody solution.

(3) Administration Amount and Administration Method

Physiological saline (control group) or the anti-GIP antibody solution (0.5 mg/kg body weight) (anti-GIP antibody administration group) was intraperitoneally administered to C57BL/6J mice (107-week-old) once a week (9:00 to 10:00 a.m.), 8 times (8 weeks) in total.

(4) Rotarod (Motor Control Function) Test

The motor control function (the accommodation ability reflecting balance ability and agility) was evaluated by measuring the capacity of staying on a rod rotating at various speeds using a rotarod (MK-600A, manufactured by Muromachi Kikai Co., Ltd.). The test was performed for 50-week-old mice (non-administration group) and 115-week-old mice (non-administration group, control group, and anti-GIP antibody administration group). Each mouse was placed on a stationary rod, and the number of times of falling was measured with a program of 6 rpm (1 min)→12 rpm (1 min)→16 rpm (1 min)→20 rpm (1 min)→24 rpm (1 min)→28 rpm (1 min).

(5) Statistical Analysis

The analysis results were shown as the average value (Ave.)±standard error (SE). The statistical analysis was performed using 2-way ANOVA followed by Bonferroni's post hoc test, and the difference was judged to be statistically significant when the P value was 0.05 or less.

(6) Results

Figure 4:
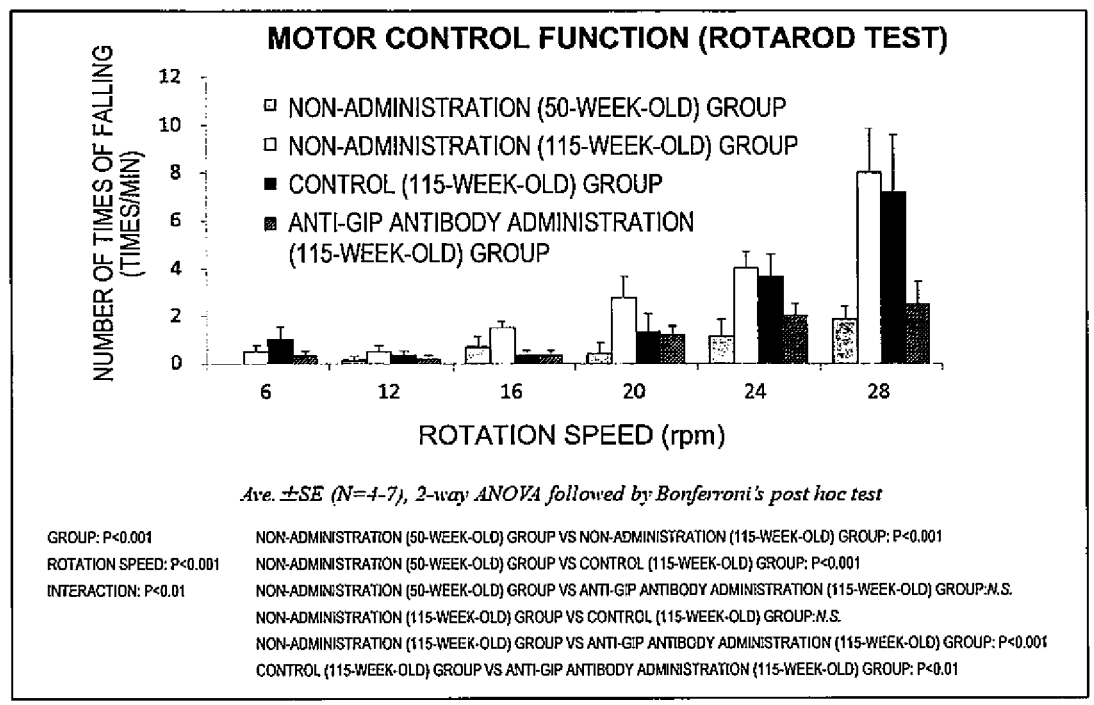
FIG. 4 is a graph showing changes in the motor control function by continuous administration of an anti-GIP antibody to aged mice.

A significant decrease in the motor control function (an increase in the number of times of falling with an increase of the rotation speed) was observed in the non-administration (115-week-old) group and the control (115-week-old) group compared to the non-administration (50-week-old) group. In the anti-GIP antibody administration (115-week-old) group, improvement in the motor control function was observed compared to the non-administration (115-week-old) group and the control (115-week-old) group, and the motor control function was equivalent to that of the non-administration (50-week-old) group (FIG. 4).

Example 4: Motor Control Function Improving Activity of GIP Secretion- or Increase-Suppressing Agent on Aged Mouse (1) Animal and Breeding Method Four-week-old C57BL/6J male mice (CLEA Japan, Inc.) were transferred (room temperature: 23° C., humidity: 55±10%, light period: 7:00 to 19:00) and were fed with food and water ad libitum. The mice were fed with high fat diet (D12451, Research Diets, Inc.) for 57 weeks (up to 61-week-old) and were then grouped such that the body weights of each group were respectively equivalent to each other. The mice were fed with high fat diet containing 30% lipid (high fat diet group), 30% high fat diet containing 20% common mushroom squeeze (common mushroom intake group), or 30% high fat diet containing 30% wheat bran (wheat bran intake group) as experimental diet for 9 weeks (70-week-old). During the breeding period, the body weight was measured once a week, and the food intake amount was measured 3 times a week. During the breeding period, the intake of the food and water was free. The motor control function was measured at 70-week-old by a rotarod test.

(2) Preparation of Food and Composition Ratio

The fruiting body (11.3 kg) of common mushroom (*Agaricus bisporus*) was squeezed with a slow juicer (HUROM Group Corporation) under room temperature conditions and a squeeze liquid was then lyophilized to prepare a common mushroom squeeze powder (308.2 g).

Wheat bran purchased from Nisshin Pharma Inc. was steam-treated with an extruder (EA-20, SUEHIRO EPM CORPORATION) and was then mixed with water in an amount equivalent to 35% of the weight of the wheat bran, and the mixture was treated with the extruder under conditions of 120° C. and 5.0 MPa to use the resultant as steamed wheat bran.

The ingredient compositions of the common mushroom squeeze and the steamed wheat bran were analyzed by a food composition analytical center. The composition ratios of the common mushroom squeeze and the steamed wheat bran are shown in Table 1 and Table 2. The composition ratio of each food used in the test is shown in Table 3. The food containing a common mushroom squeeze or the wheat bran was prepared, in consideration of the composition of each ingredient, by replacing ingredients with the common mushroom squeeze or the wheat bran such that the nutritional composition and calorie were equivalent to those of the high fat diet as the control.

TABLE 1

Ingredient composition of common mushroom squeeze

| Common mushroom squeeze | g/100 g |
|---|---|
| Carbohydrate | 41.2 |
| Lipid | 2.1 |
| Protein | 34.4 |
| Dietary fiber | 9.4 |
| Ash | 11.4 |
| Moisture | 1.5 |

TABLE 2

Ingredient composition of steamed wheat bran

| Steamed wheat bran | g/100 g |
|---|---|
| Carbohydrate | 20.2 |
| Lipid | 4.2 |
| Protein | 18.9 |
| Dietary fiber | 47.9 |
| Ash | 6.5 |
| Moisture | 2.3 |

TABLE 3

Dietary composition of food

| | Control | Common mushroom | Wheat bran |
|---|---|---|---|
| Corn oil | 25 | 24.54 | 23.64 |
| Lard | 5 | 4.96 | 4.90 |
| Pregelatinized potato starch | 28.5 | 19.28 | 11.96 |
| Sucrose | 13 | 12.96 | 12.90 |
| Casein | 20 | 13.08 | 14.23 |
| Cellulose | 4 | 3.02 | 0 |
| Mineral mixture | 3.5 | 1.18 | 1.45 |
| Vitamin mixture | 1 | 0.96 | 0.90 |
| Common mushroom squeeze | 0 | 20 | 0 |
| Steamed wheat bran | 0 | 0 | 30 |

The contents in experimental diet are expressed in percentage (w/w).

(3) Rotarod (Motor Control Function) Test

The motor control function (the accommodation ability reflecting balance ability and agility) was evaluated by measuring the capacity of staying on a rod rotating at various speeds using a rotarod (MK-600A, manufactured by Muromachi Kikai Co., Ltd.). Each mouse was placed on a stationary rod, and the time until falling and the rotation speed at the time of falling were measured with a program of 6 rpm (1 min)→12 rpm (1 min)→16 rpm (1 min)→20 rpm (1 min).

(4) Statistical Analysis

The analysis results were shown as the average value (Ave.)±standard error (SE). The statistical analysis was performed using 1-way ANOVA followed by Dunnett's post hoc test, and the difference was judged to be statistically significant when the P value was 0.05 or less.

(5) Results

Figure 5:
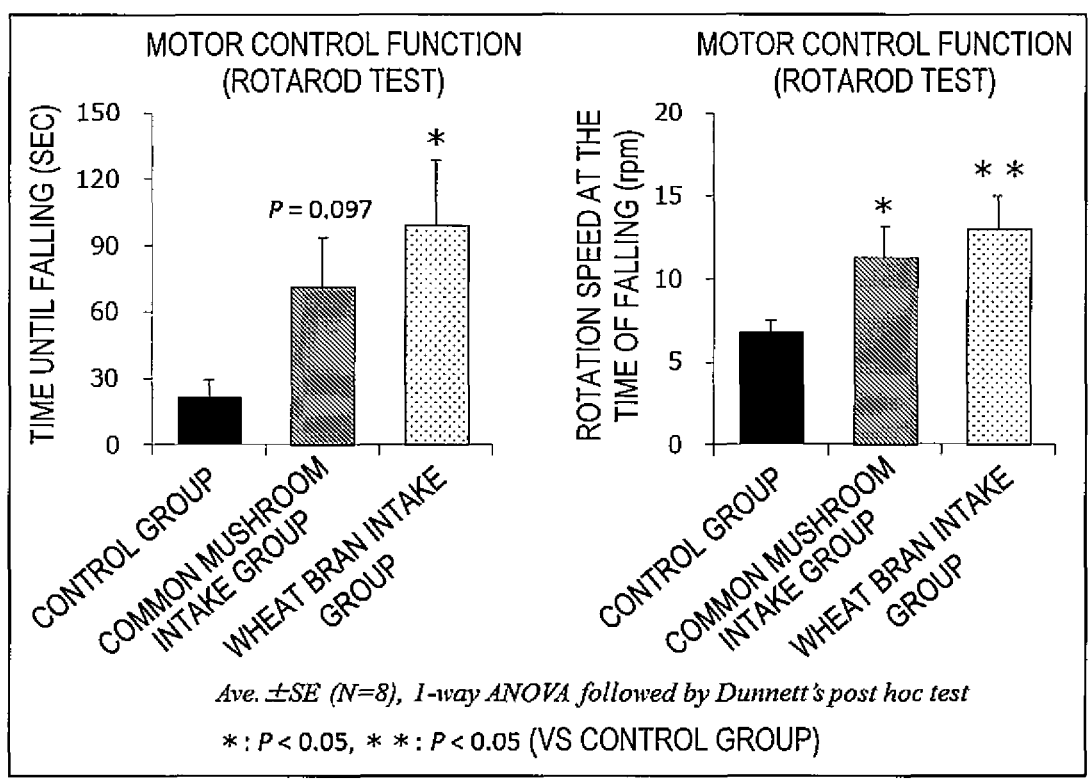
FIG. 5 is a graph showing the motor control function improving activity of GIP increase-suppressing agent on aged mice.

Motor control function improving activity was observed in the group of continuously taking in a GIP secretion- or increase-suppressing agent (common mushroom or wheat bran) compared to the control group (FIG. 5).

The invention claimed is:

1. A method for improving a subject's agility, the method comprising administering a Glucose-Dependent Insulinotropic Polypeptide (GIP) function inhibitor to a subject in need thereof, thereby improving the subjects agility, wherein the GIP function inhibitor is a GIP secretion- or increase-suppressing agent, and wherein the GIP secretion- or increase-suppressing agent is an extract of common mushroom (*Agaricus bisporus*).

2. A method for improving a subjects agility, the method comprising administering a Glucose-Dependent Insulinotropic Polypeptide (GIP) function inhibitor to a subject in need thereof, thereby improving the subjects agility, wherein the GIP function inhibitor is a GIP secretion- or increase-suppressing agent, and wherein the GIP secretion- or increase-suppressing agent is a squeeze of common mushroom (*Agaricus bisporus*).

* * * * *